United States Patent
Govari et al.

(10) Patent No.: US 9,375,269 B2
(45) Date of Patent: Jun. 28, 2016

(54) CATHETER WITH INTEGRATED FLOW SENSOR

(71) Applicant: BIOSENSE WEBSTER (ISRAEL), LTD., Yokneam (IL)

(72) Inventors: Assaf Govari, Haifa (IL); Mikhael Feldchtein, Kiryat Yam (IL); Alexander Kiselman, Yokneam Illit (IL); Yaron Ephrath, Karkur (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 290 days.

(21) Appl. No.: 13/948,340

(22) Filed: Jul. 23, 2013

(65) Prior Publication Data

US 2015/0032102 A1 Jan. 29, 2015

(51) Int. Cl.
*A61B 18/14* (2006.01)
*A61B 18/00* (2006.01)

(52) U.S. Cl.
CPC ... *A61B 18/1492* (2013.01); *A61B 2018/00029* (2013.01); *A61B 2018/00577* (2013.01); *A61B 2018/00714* (2013.01); *A61B 2018/00744* (2013.01); *A61B 2018/00821* (2013.01); *A61B 2018/00863* (2013.01); *A61B 2218/002* (2013.01)

(58) Field of Classification Search
CPC ........ A61B 18/04; A61B 18/08; A61B 18/10; A61B 18/12; A61B 18/1266; A61B 18/14; A61B 18/1442; A61B 18/1445; A61B 18/1448; A61B 18/1492; A61B 2018/00029; A61B 2018/00577; A61B 2018/00714; A61B 2018/00744; A61B 2018/00821; A61B 2018/00863

USPC ..................................................... 606/41–50
See application file for complete search history.

(56) References Cited

U.S. PATENT DOCUMENTS

| | | | |
|---|---|---|---|
| 4,464,172 A | 8/1984 | Lichtenstein | |
| 5,807,395 A | 9/1998 | Mulier | |
| 6,226,542 B1 | 5/2001 | Reisfeld | |
| 6,301,496 B1 | 10/2001 | Reisfeld | |
| 6,814,733 B2 | 11/2004 | Schwartz | |
| 6,892,091 B1 | 5/2005 | Ben-Haim | |
| 6,997,924 B2 | 2/2006 | Schwartz | |
| 7,156,816 B2 | 1/2007 | Schwartz | |
| 7,387,625 B2 * | 6/2008 | Hovda | A61B 18/1482 606/32 |
| 7,397,364 B2 | 7/2008 | Govari | |
| 7,536,218 B2 | 5/2009 | Govari | |
| 7,756,576 B2 | 7/2010 | Levin | |
| 2003/0176833 A1 | 9/2003 | Libermann | |
| 2005/0256447 A1 | 11/2005 | Richardson | |
| 2008/0269737 A1 | 10/2008 | Elmouelhi | |
| 2010/0030209 A1 | 2/2010 | Govari | |

* cited by examiner

*Primary Examiner* — Michael Peffley
*Assistant Examiner* — Khadijeh Vahdat
(74) *Attorney, Agent, or Firm* — Notaro, Michalos & Zaccaria P.C.

(57) ABSTRACT

Methods and systems facilitate catheterization of a living subject by passing a fluid through an irrigation conduit. Heat energy is delivered to the conduit to create a heated pod of irrigation fluid that propagates downstream from the heat source. A departure time of the pod from a first location in the conduit is recorded, and an arrival time of the pod is detected at a second location that is downstream from the first location. A transit time of the pod from the first location to the second location is determined, and the flow of the fluid is adjusted responsively to the transit time.

9 Claims, 3 Drawing Sheets

CATHETER WITH INTEGRATED FLOW SENSOR

BACKGROUND OF THE INVENTION

1. Field of the Invention

This invention relates to tissue ablation systems. More particularly, this invention relates to monitoring of flow rates of irrigation fluid within an invasive probe within the body.

2. Description of the Related Art

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy, e.g., radiofrequency energy, via a catheter, it is sometimes possible to cease or modify the propagation of unwanted electrical signals from one portion of the heart to another. The ablation process destroys the unwanted electrical pathways by formation of non-conducting lesions.

A known difficulty in the use of radiofrequency energy for cardiac tissue ablation is controlling local heating of tissue. There are tradeoffs between the desire to create a sufficiently large lesion to effectively ablate an abnormal tissue focus, or block an aberrant conduction pattern, and the undesirable effects of excessive local heating. If the radiofrequency device creates too small a lesion, then the medical procedure could be less effective, or could require too much time. On the other hand, if tissues are heated excessively then there could be local charring effects due to overheating. Such overheated areas can develop high impedance, and may form a functional barrier to the passage of heat. The use of slower heating provides better control of the ablation, but unduly prolongs the procedure.

Previous approaches to controlling local heating include the inclusion of thermocouples within the electrode and feedback control, signal modulation, local cooling of the catheter tip, and fluid-assisted techniques, for example irrigation of the target tissue during the energy application, using chilled fluids. Typical of the last approach is Mulier, et al. U.S. Pat. No. 5,807,395.

Commonly assigned U.S. Pat. No. 6,997,924, which is herein incorporated by reference, describes a technique of limiting heat generated during ablation by determining a measured temperature of the tissue and a measured power level of the transmitted energy, and controlling the power output level responsively to a function of the measured temperature and the measured power level.

More recently, commonly assigned U.S. Patent Application Publication No. 2010/0030209 by Govari et al., which is herein incorporated by reference, describes an insertion tube, having an outer surface with a plurality of perforations through the outer surface, which are typically about 100 µm in diameter, and are distributed circumferentially and longitudinally over the distal tip. A lumen passes through the insertion tube and is coupled to deliver an irrigation and cooling fluid to the tissue via the perforations.

SUMMARY OF THE INVENTION

There is provided according to embodiments of the invention a method of catheterization, which is carried out by inserting a catheter into a body of a living subject, causing a flow of a fluid through an irrigation conduit. The method is further carried out by delivering heat energy to the conduit from a heat source that is external to the conduit to create a heated pod of irrigation fluid that propagates downstream from the heat source, recording a departure time of the pod from a first location in the conduit, detecting externally to the conduit an arrival time of the pod at a second location that is downstream from the first location, determining a transit time of the pod from the first location to the second location measured by the departure time and the arrival time, and adjusting the flow of the fluid responsively to the transit time.

In a further aspect of the method, the catheter has an ablation electrode. The method is further carried out by actuating the ablation electrode to deliver energy to an ablation site.

According to yet another aspect of the method, detecting the arrival time is performed by recording signals from the first and second thermocouples to determine passage of the pod by their respective first and second locations.

According to still another aspect of the method, the first location corresponds to a location of the heat source and the second location corresponds to a location of a thermocouple, and detecting is performed by recording temperature signals from the thermocouple to determine passage of the pod by the second location responsively to the temperature signals.

In another aspect of the method adjusting the flow is performed by establishing an objective that is representative of a desired flow through the conduit, calculating a deviation from the objective based on the transit time, and adjusting the flow to reduce the deviation.

According to an additional aspect of the method, the objective is a desired transit time between the first location and the second location.

In one aspect of the method, adjusting the flow is carried out by establishing a desired flow through the conduit, calculating an actual flow based on the transit time, determining a deviation between the desired flow and the actual flow, and adjusting the flow to reduce the deviation.

There is further provided according to embodiments of the invention an ablation apparatus, including a flexible catheter adapted for insertion into a heart of a living subject and having an ablation electrode disposed at the distal segment of the catheter, which can be brought into contact with a target tissue in the heart. The catheter has a lumen for passage of irrigation fluid therethrough, the fluid exiting from the catheter at the distal segment for cooling of the target tissue. The apparatus includes an ablator, operative to apply a dosage of energy to the target tissue to ablate the target tissue, a flow processor for adjusting a flow of the irrigation fluid through the lumen, and a sensor unit, disposed in a non-contacting relationship with the irrigation fluid, including a heat source that delivers heat energy to the irrigation fluid flowing in the lumen, and a thermocouple disposed downstream from the heat source in a direction of flow of the irrigation fluid for measuring a temperature of the irrigation fluid.

According to one aspect of the apparatus, the sensor unit is external to the lumen.

According to yet another aspect of the apparatus, the sensor unit is disposed in the handle of the catheter.

A further aspect of the apparatus includes a controller operative for energizing the heat source of the sensor unit for a predetermined time interval to create a heated pod of irrigation fluid that propagates downstream from the heat source, recording a departure time of the pod from a first location, detecting a temperature signal from the thermocouple indicative of a change in the temperature of the irrigation fluid, determining an arrival time of the pod at a second location responsively to the temperature signal, determining a transit time of the pod from the first location to the second location measured by the departure time and the arrival time, and commanding the flow processor to adjust the flow of the irrigation fluid responsively to the transit time.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Figure 1:
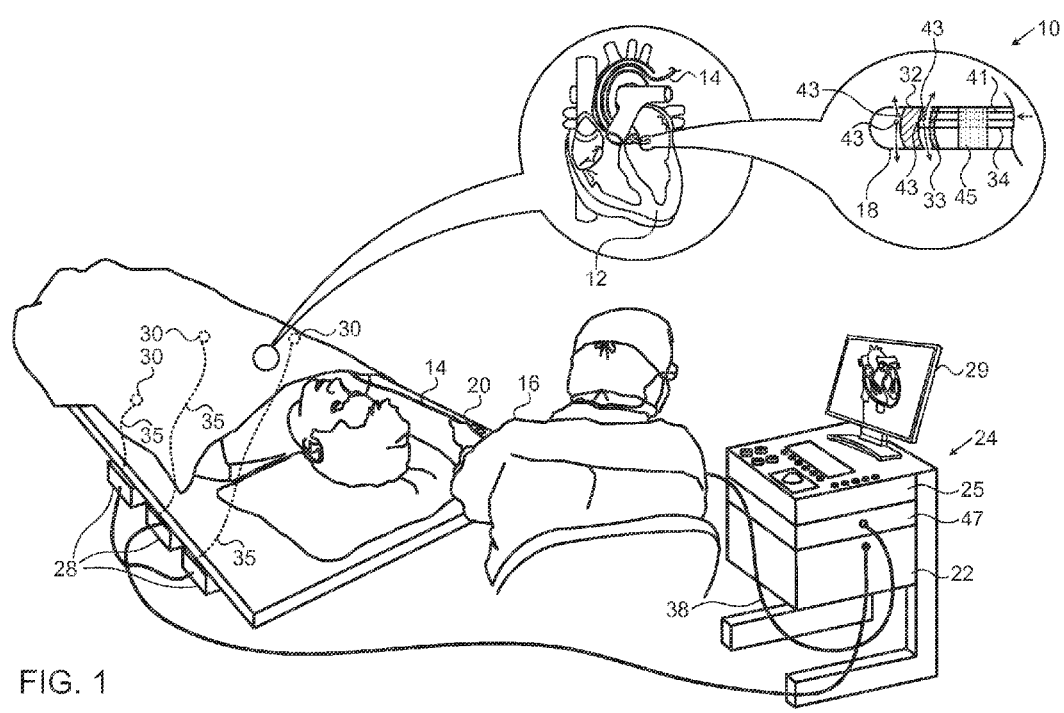
FIG. 1 is a pictorial illustration of a system for performing diagnostic and therapeutic procedures on a heart of a living subject, which is constructed and operative in accordance with an embodiment of the invention.

Turning now to the drawings, reference is initially made to FIG. 1, which is a pictorial illustration of a system 10 for performing diagnostic and therapeutic procedures on a heart 12 of a living subject, and which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall at an ablation target site. Optionally, electrical activation maps may then be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a positioning processor 22, located in a console 24.

Ablation energy and electrical signals can be conveyed to and from the heart 12 through one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24, are disposed between the ablation electrodes 32 and have connections to the cable 34.

Wire connections 35 link the console 24 with body surface electrodes 30 and other components of a positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

The positioning processor 22 is an element of a positioning subsystem in the system 10 that measures location and orientation coordinates of the catheter 14.

In one embodiment, the positioning sub-system comprises a magnetic position tracking arrangement that determines the position and orientation of the catheter 14 by generating magnetic fields in a predefined working volume and sensing these fields at the catheter, using field generating coils 28. The positioning subsystem may employ impedance measurement, as taught, for example in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14 and to analyze the electrical signals from the electrodes.

A lumen or conduit 41 within the catheter 14 conducts irrigation and cooling fluid to the tip of the catheter, where it exits via apertures 43, which are located near the ablation electrode 32. The fluid serves to cool the tissues during ablation in order to prevent the undesirable effects mentioned above. Temperature control of the ablation site is facilitated by regulating the rate and hence volume of flow through the conduit 41 and the apertures 43. A higher flow rate cools the area more than a lower flow rate. A flow sensor module 45 measures the flow rate and transmits signals indicating the measurement to the console 24, for example via the cable 34. A controller in the console 24 responds to the signals and varies the volume of fluid flowing through the conduit 41. In FIG. 1 the flow sensor module 45 is disposed distally in the catheter 14. This is not essential, and the flow sensor module 45 can be located anywhere along the course of the conduit 41, for example within the handle 20 of the catheter 14 (FIG. 1). A controller 47 monitors the flow sensor module 45 and sends control signals that cause adjustment of irrigation fluid, for example, by commanding a pump, pump controller or other flow rate device known in the art (not shown).

Typically, the system 10 includes other elements, which are not shown in the figures for the sake of simplicity. For example, the system 10 may include an electrocardiogram (ECG) monitor, coupled to receive signals from one or more body surface electrodes, to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. As noted above, conventional pumps and lines for circulating liquids through the catheter 14 for cooling the ablation site are provided.

Figure 2:
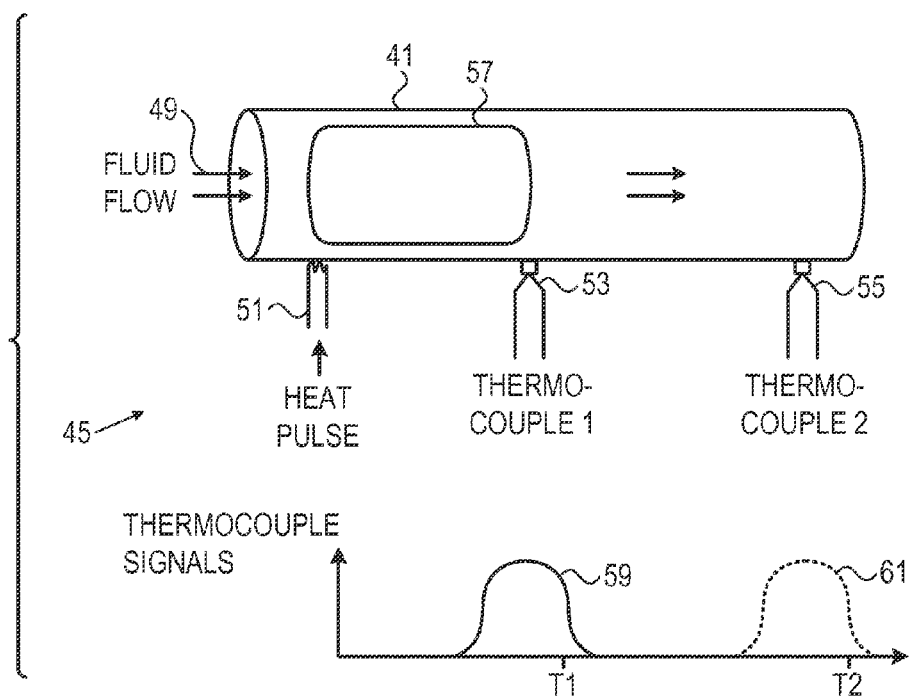
FIG. 2 is a detailed schematic view of the flow sensor module shown in FIG. 1 in accordance with an embodiment of the invention.

Reference is now made to FIG. 2, which is a detailed schematic view of the flow sensor module 45 (FIG. 1), which is constructed and operative in accordance with an embodiment of the invention. It will be noted that the components of the flow sensor module 45 described below are all in a non-contacting relationship with irrigation fluid 49 in the conduit. In FIG. 2 they are all external to the conduit 41, and do not contact irrigation fluid 49 within the conduit 41. In some embodiments in which the flow sensor module 45 is disposed in the interior of the catheter 14 (FIG. 1) or a lumen within the catheter 14, a suitable seal may be provided to prevent contact with irrigation fluid. A heating element 51 can be realized as a resistor in contact with the external wall of the conduit 41. The resistor may be a simple coil wound around the conduit 41. Two thermocouples 53, 55, spaced at different distances from the heating element 51, are attached to the wall of the conduit 41 on downstream from the heating element 51. Typically, the thermocouples 53, 55 are spaced apart by 0.5-2 mm.

The controller 47 (FIG. 1) energizes the heating element 51 for a short time (typically 0.5-2 sec), thereby providing a "heat pulse" to the irrigation fluid 49 flowing in the conduit 41. The heat pulse raises the temperature of the fluid in proximity to the heating element 51, forming a localized fluid pod or cell 57, which has an increased temperature relative to fluid outside the pod, and which flows downstream within the conduit 41, tending to maintain its identity, at least in the interval between the thermocouples 53, 55.

In the example of FIG. 2, plots of the signals developed by the thermocouple 53, 55 over time are shown as curves 59, 61, respectively. Transient rises in signal strength from the thermocouples 53, 55 can be detected using conventional pulse detection circuitry (not shown) or by software in the controller 47 (FIG. 1).

The cell 57 arrives at the thermocouple 53 at time t1, and increased fluid temperature is detected by the thermocouple 53, as shown by the curve 59. Then, at time t2 the cell 57 arrives at the thermocouple 55, which develops a transient signal as shown by the curve 61. Rises in signal strength are determined by the controller 47, which then registers the times at which the cell 57 passes each of the thermocouples 53, 55. The time difference (t2−t1) between corresponding points, e.g., half maxima of the curves 59, 61, correlates inversely with rate of flow of the cell 57. Moreover, the propagation of the cell 57 through the conduit 41 is representative of the rate of flow of the irrigation fluid 49 generally in the conduit 41, so that the time difference (t2−t1) also correlates inversely with the fluid volume passing through the conduit 41. Flow rates of about 2 m/sec are typical.

The components of the flow sensor module 45 are very small, and, as noted above, can be fitted into catheter itself, e.g., the handle 20 (FIG. 1). It will be appreciated by those skilled in the art that conventional cardiac catheters and their irrigation systems may be readily retrofitted by addition of the flow sensor module 45. Versions of the flow sensor module 45 that employ wireless transmission are particularly suitable to upgrades of such catheters, as no additional wires need be installed. Placing the flow sensor module 45 in the catheter 14 is advantageous, as it facilitates detection of tube kink, a condition which commonly occurs during the procedure.

Although the curves 59, 61 are separated by an interval in FIG. 2, this is not necessarily the case. Overlap can be tolerated if the signals from the thermocouples 53, 55 can be differentiated from one another. For example, the thermocouples 53, 55 may report to the controller 47 on separate lines, or even by known methods of wireless communication as described, e.g., in commonly assigned U.S. Pat. No. 7,397,364 to Govari, entitled "Digital Wireless Position Sensor", which is herein incorporated by reference.

Alternate Embodiment

Since energizing the heating element is implemented by the controller, the controller is aware of the time of energizing. The controller may use this time determination to improve the estimate of the speed and flow rate of the fluid. Alternatively, rather than using two thermocouples, only one may be used.

Figure 3:
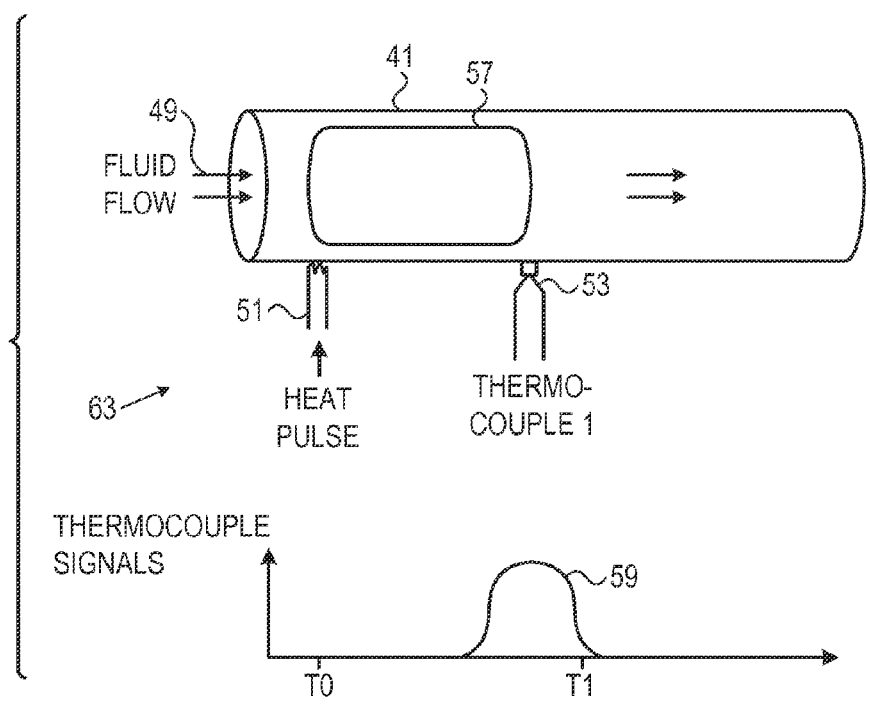
FIG. 3, which is a detailed schematic view of the flow sensor module shown in FIG. 1 in accordance with an alternate embodiment of the invention.

Reference is now made to FIG. 3, which is a detailed schematic view of a flow sensor module 63, in accordance with an alternate embodiment of the invention. The construction of the flow sensor module 63 is generally similar to the flow sensor module 45 (FIG. 2), except now the thermocouple 55 is omitted, and reliance is placed on the thermocouple 53 to indicate a change in temperature as the cell 57 flows downstream from the heating element 51.

In this version the heating element 51 is energized for a time interval beginning at time t0, which, as noted above, is known to the controller 47 (FIG. 1). The cell 57 forms during the interval and its leading edge arrives at the thermocouple 53 at time t1. Increased fluid temperature is detected using the signal from the thermocouple 53, as in the previous embodiment, indicated by the curve 59. Flow rate is measured as in the previous embodiment, but using the time difference (t1−t0). Calibration data is prepared as described above.

Operation

Figure 4:
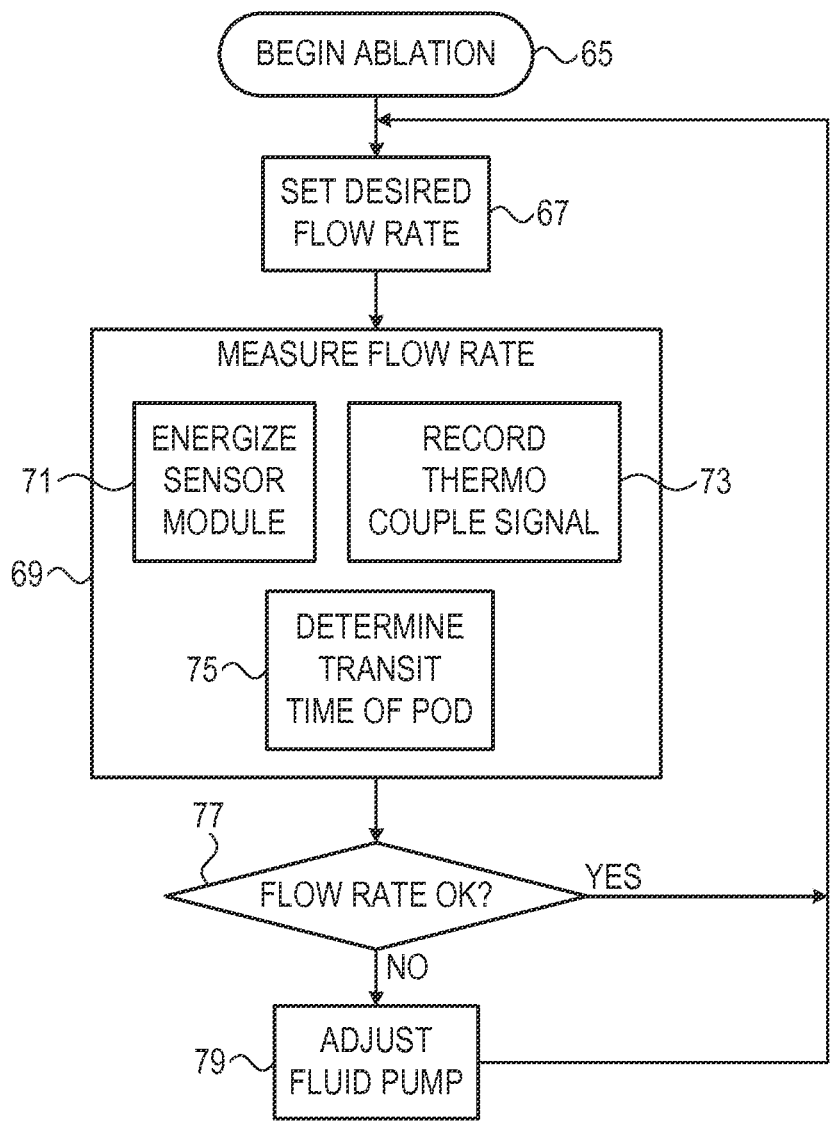
FIG. 4 is a flow chart of a method for monitoring flow rates of irrigation fluid in a cardiac catheter in accordance with an embodiment of the invention.

Reference is now made to FIG. 4, which is a flow chart of a method for monitoring flow rates of irrigation fluid in a cardiac catheter in accordance with an embodiment of the invention. The method is suitable for any of the embodiments discussed above.

The process begins at initial step 65. It is assumed that a subject has been catheterized, and the ablation electrode of the catheter positioned at a target site. Then, at step 67, an objective representing an optimum flow rate is determined. The objective may be some parameter representative of flow rate, for example a transit time of the fluid between two points or an actual flow rate. The parameter may be derived, for example, from an optimum temperature of the ablation site. The optimum flow rate usually varies dynamically during the procedure, and may be responsive, for example, to the tissue temperature of the ablation site, and to other factors, such as limitations on fluid loading of the subject. The details of this step are beyond the scope of this disclosure and are not further discussed. Additionally or alternatively an optimum transit time interval for propagation of the pod described above may be established. This may be achieved by reference to a previously constructed a transit time table or function, which correlates with flow rates through the irrigation conduit.

Next, at step 69 the flow rate is measured. Step 69 comprises step 71, step 73 and step 75. In step 71 an energy pulse is delivered to a heating element to create a pod having elevated temperature relative to the general flow of irrigation fluid through the catheter. Step 73, recording a thermocouple signal is performed throughout the measurement operation, at least until a rise in temperature is detected, thereby indicating arrival of the pod the thermocouple. At step 75, the transit time between the heating element and the thermocouple is determined and may be correlated with previously determined flow rate table, or function.

Next, at decision step 77, it is determined if the flow rate or transit time measured in step 69 is within tolerance limits with respect to the desired flow rate or transit time that was set in the last performance of step 67. If the determination is affirmative, then control returns to step 67, where the currently required flow rate or transit time is redetermined as described above.

If the determination at decision step 77 is negative then control proceeds to step 79. A pump or other adjusting mechanism is corrected to null out the difference between the measurement obtained in step 69 and the objective that was established in step 67. Control then returns to step 67.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An ablation apparatus, comprising:
a flexible catheter adapted for insertion into a heart of a living subject and having a distal segment and an ablation electrode disposed at the distal segment to be brought into contact with a target tissue in the heart, the flexible catheter having a lumen for passage of irrigation fluid therethrough to an exit from the flexible catheter at the distal segment for cooling of the target tissue;
an ablator, operative to apply a dosage of energy to the target tissue to ablate the target tissue;
a flow processor for adjusting a flow of the irrigation fluid through the lumen;
a sensor unit, disposed in a non-contacting relationship with the irrigation fluid, comprising a heat source that delivers heat energy to the irrigation fluid flowing in the lumen and a thermocouple disposed downstream from the heat source in a direction of flow of the irrigation fluid for measuring a temperature of the irrigation fluid; and
a controller operative for:
energizing the heat source of the sensor unit for a predetermined time interval to create a heated pod of irrigation fluid that propagates downstream from the heat source;
recording a departure time of the heated pod from a first location;
detecting a temperature signal from the thermocouple indicative of a change in the temperature of the irrigation fluid;
determining an arrival time of the heated pod at a second location responsively to the temperature signal;
determining a transit time of the heated pod from the first location to the second location measured by the departure time and the arrival time; and
commanding the flow processor to adjust the flow of the irrigation fluid responsively to the transit time.

2. The apparatus according to claim 1, wherein the sensor unit is external to the lumen.

3. The apparatus according to claim 1, wherein the flexible catheter has a handle, and the sensor unit is disposed in the handle.

4. The apparatus according to claim 1, wherein the controller is operative for performing the steps of energizing, recording, detecting, determining a transit time, and commanding while the ablation electrode is actuated.

5. The apparatus according to claim 1, wherein the first location corresponds to a location of the thermocouple and the second location corresponds to a location of another thermocouple, and detecting is performed by recording signals from the thermocouple and the other thermocouple to determine passage of the heated pod by the first and second locations.

6. The apparatus according to claim 1, wherein the first location corresponds to a location of the heat source and the second location corresponds to a location of the thermocouple, and detecting is performed by recording temperature signals from the thermocouple to determine passage of the heated pod by the second location.

7. The apparatus according to claim 1, wherein commanding the flow processor comprises the steps of:
establishing an objective that is representative of a desired flow through the lumen;
calculating a deviation from the objective based on the transit time; and
transmitting control signals to the flow processor to adjust the flow to reduce the deviation.

8. The apparatus according to claim 7, wherein the objective is a desired transit time between the first location and the second location.

9. The apparatus according to claim 1, wherein commanding the flow processor comprises the steps of:
establishing a desired flow through the lumen;
calculating an actual flow based on the transit time;
determining a deviation between the desired flow and the actual flow; and
transmitting control signals to the flow processor to adjust the flow to reduce the deviation.

* * * * *